(12) United States Patent
Wagner et al.

(10) Patent No.: US 6,193,762 B1
(45) Date of Patent: Feb. 27, 2001

(54) SURFACE FOR USE ON AN IMPLANTABLE DEVICE

(75) Inventors: Donald J. Wagner, Venetia; Gary Reed, Clairton, both of PA (US)

(73) Assignees: Cycam, Inc., Houston; Tech Met, Inc., Glassport, both of PA (US)

( * ) Notice: Subject to any disclaimer, the term of this patent is extended or adjusted under 35 U.S.C. 154(b) by 0 days.

(21) Appl. No.: 09/324,695

(22) Filed: Jun. 2, 1999

Related U.S. Application Data (60) Division of application No. 08/785,983, filed on Jan. 22, 1997, now Pat. No. 5,922,029, which is a continuation-in-part of application No. 08/588,790, filed on Jan. 19, 1996, now abandoned, which is a continuation of application No. 08/358,045, filed on Dec. 15, 1994, now Pat. No. 5,507,815, which is a continuation of application No. 08/122,254, filed on Sep. 15, 1993, now abandoned, which is a continuation of application No. 07/716,167, filed on Jun. 17, 1991, now abandoned.

(51) Int. Cl.[7] ................. A61F 2/02; B44C 1/22

(52) U.S. Cl. ............................. 623/66; 205/656

(58) Field of Search ................. 204/224, 151; 438/924, 694; 205/653–656; 623/920, 11.11, 66; 427/2

(56) References Cited

U.S. PATENT DOCUMENTS

| | | |
|---|---|---|
| 3,650,861 | 3/1972 | Angell . |
| 3,891,456 | 6/1975 | Hohman et al. . |
| 3,995,371 | 12/1976 | O'Keefe . |
| 4,116,755 | 9/1978 | Coggins et al. . |
| 4,272,855 | 6/1981 | Frey . |
| 4,314,876 | 2/1982 | Kremer et al. . |
| 4,330,891 | 5/1982 | Branemark et al. . |
| 4,414,039 | 11/1983 | Thoma . |
| 4,540,465 | 9/1985 | Coggins et al. . |
| 4,588,480 | 5/1986 | Thoma . |
| 4,644,942 | 2/1987 | Sump . |
| 4,673,409 | 6/1987 | Van Kampen . |
| 4,803,098 | 2/1989 | Henri et al. . |
| 4,834,756 | 5/1989 | Kenna . |
| 4,836,884 | 6/1989 | McAuslan . |
| 4,846,837 | 7/1989 | Kurze et al. . |
| 4,863,475 | 9/1989 | Andersen et al. . |

(List continued on next page.)

OTHER PUBLICATIONS

Metals Handbook, Ninth Edition, vol. 16, Machining, pp. 533–541, ASM International, Mar. 1989.

*Primary Examiner*—David J. Isabella
(74) *Attorney, Agent, or Firm*—Barry I. Friedman; Metz Schermer & Lewis, LLC (57) ABSTRACT

An attachment surface for an implantable device has a random irregular pattern formed through a repetitive masking and chemical milling process. Additionally, an attachment surface for an implantable device has a random irregular pattern formed through a repetitive masking and electrochemical milling process. The electrochemical milling process is particularly well suited for use with substrate materials which have high chemical inertness which makes them resistant to chemical etching. Surface material is removed from the implant surface without stress on the adjoining material and the process provides fully dimensional fillet radii at the base of the surface irregularities. This irregular surface is adapted to receive the ingrowth of bone material and to provide a strong anchor for that bone material. The unitary nature of the substrate and surface features provides a strong anchoring surface with is resistant to cracking or breaking. The surface is prepared through an etching process which utilizes the random application of a maskant and subsequent etching of the metallic substrate in areas unprotected by the maskant. This chemical etching process is repeated a number of times as necessitated by the nature of the irregularities required in the surface. The etching characteristics are controlled by the time, temperature and number of repetitions utilized in the etching process.

33 Claims, 4 Drawing Sheets

U.S. PATENT DOCUMENTS

| | | |
|---|---|---|
| 4,865,603 | 9/1989 | Noiles . |
| 4,900,398 | 2/1990 | Chen . |
| 4,944,763 | 7/1990 | Willert et al. . |
| 4,955,909 | 9/1990 | Ersek et al. . |
| 4,978,358 | 12/1990 | Bobyn . |
| 5,002,572 | 3/1991 | Picha . |
| 5,002,580 | 3/1991 | Noble et al. . |
| 5,158,571 | 10/1992 | Picha . |
| 5,246,530 | 9/1993 | Bugle et al. . |
| 5,507,815 | 4/1996 | Wagner et al. . |
| 5,853,561 | 12/1998 | Banks . |

SURFACE FOR USE ON AN IMPLANTABLE DEVICE

CROSS REFERENCE TO RELATED APPLICATION

This application is a continuation-in-part of Wagner, et al., a application similarly titled, bearing Ser. No. 08/785,938, filed Jan. 22, 1997, now U.S. Pat. No. 5,922,029 which is a continuation-in-part of Wagner, et al., Ser. No. 08/588,790, filed Jan. 19, 1996 now abandoned, which in turn is a continuation of Wagner, et al., Ser. No. 08/358,045, filed Dec. 15, 1994, now U.S. Pat. No. 5,507,815, which was a continuation of Wagner, et al., Ser. No. 08/122,254, filed Sep. 15, 1993, now abandoned, which was a continuation of Wagner, et al., Ser. No. 07/716,167, filed Jun. 17, 1991, also now abandoned.

BACKGROUND OF THE INVENTION

1. Field of the Invention

The present invention relates to an irregular surface which is utilized on a bone implant to facilitate the growth of bone tissue within the surface. The invention also relates to a method of production of this surface. The invention further relates to an irregular surface which is utilized on a substrate material to particularly adapt that surface for joining to a second material. More specifically, the invention relates to the sequential etching of a bone implant surface to produce an irregular random pattern of protrusions and depressions through the use of chemical and electrochemical milling techniques.

2. Description of the Prior Art

In the field of bone implantation, or the use of man-made objects to replace portions of bone within the human body, there are two primary methods of affixing the implant device to the existing bone. The first of these methods involves the use of a cement or adhesive material which is applied to the surfaces of the implant and the bone. The cement is adapted to harden in a rapid fashion and rigidly affix the two portions in an immobile manner. The use of cement permits the application of loads to the joinder of the bone and the implant within a relatively short time following implantation. This is generally desirable in terms of the well-being of the patient, in that a quick physical recovery improves the overall recovery of the patient.

One of the significant shortcomings of a cement adhesion of the two elements is that over time, the cement tends to deteriorate. This deterioration may permit relative movement between the implant and the bone surface and if untreated, could allow the two joined elements to separate. In either event, the result is painful and dangerous to the patient.

A second method of affixation of the implant to the bone has also been utilized as an alternative to the cement technique. In this embodiment, the implant is provided with an irregular surface into which the bone may grow, creating a natural joinder between the bone and the implant. One of the shortcomings of this implantation technique, however, is the longer recovery time necessary to permit ingrowth of the bone into the surface of the implant. An additional problem which has occurred with relation to the ingrowth embodiment relates to the preparation of the surface of the implant. An implant having a smooth surface is inappropriate for use in this type of operation as it provides no gripping surface for the bone. An irregular surface, therefore, is preferred and in fact necessary for this application. Several methods have been proposed in the prior art for the preparation of the surface, such that a stable gripping surface will be provided into which the bone may grow.

Frye, U.S. Pat. No. 4,272,855, issued Jun. 16, 1981, discloses the use of generally conical projections emanating from the surface of the implant. These projections may be perpendicular to the surface of the implant or may be extending outwardly at an angle between 50° and 90°, with respect to the surface of the implant Frye teaches that an increase in the anchoring surface is a decisive feature which can influence and improve the bond between tissue and the implant. The projections described in Frye are generally regular in shape and devoid of corners and edges and have transition surfaces merging into the base level.

Van Kampen, U.S. Pat. No. 4,673,409, issued Jun. 16, 1987, discloses an implant having a surface comprising a multiplicity of spaced posts projecting from the implant surface for mating with bone material. The Van Kampen reference specifically teaches away from an edgeless surface as taught by the Frye reference. Van Kampen instructs that while a rounded surface minimizes the formation of stresses, it minimizes the total surface area that may be joined to the tissue, thus reducing the strength of the implant. Van Kampen discloses the use of regular posts which are roughly rectangular in cross-section. The posts are spaced at a regular interval and are formed by laser drilling.

It is evident from the teaching of these two references that there is some disagreement in the art regarding the best approach towards the preparation of an implant surface.

Another technique in the preparation of an implant surface is disclosed in Sump, U.S. Pat. No. 4,644,942, issued Feb. 24, 1987. The Sump reference discloses the use of a coating which is applied to the surface of the implant. The coating is comprised of a solid metallic powder and a solution of organic binders. A slurry formed of the two elements is applied to the surface of the implant and is permanently affixed thereto under controlled temperature and pressure conditions. The organic material is subsequently removed, leaving a porous, metallic coating on the surface of the implant.

Other techniques for applying a similar coating include plasma spray of a metallic material onto the surface of an implant resulting in a similar metallic irregular coating. While these porous coatings do provide an attachment surface into which bone may grow, these surfaces and the surface described in Noiles, U.S. Pat. No. 4,865,603, issued Sep. 13, 1989, exhibit significant shortcomings. The Noiles reference describes a surface in which furrows and depressions are cut or stamped into the surface of the implant. Each of these surfaces involves the addition of metallic material or the manipulation of the metallic surface of the implant. Each of these methodologies provides a surface that is subject to breakage and dislocation under stress. A metallic addition to the surface of the implant, even under rigorously controlled conditions, forms a joinder which is more easily broken than a singularly formed piece of metallic substrate. Similarly, the manipulation of the surface of the implant, even though formed of a single integral metal substrate, involves the stressing of the metallic surface which forms a locus for breakage when the implant is under a load.

What is lacking in the art, therefore, is an attachment surface utilized in conjunction with a metallic bone implant which has the structural integrity of a unitary element formed without the necessity of stressing that surface through manipulation. Additionally, what is needed in the art is a surface having the irregularities provided by an applied coating without the necessary lack of strength inherent in the joinder of the coating material to the implant substrate.

SUMMARY OF THE INVENTION

An attachment surface is provided in which a random irregular pattern is formed through a repetitive masking and chemical milling process. In some applications, such as the affixation of a composite material to a rigid or metallic substrate, the malleable composite material is molded into the irregularities of the substrate. As utilized in the production of some aircraft components, for example, a malleable, composite surface material is deposited upon a metal superstructure, which provides strength and support. The composite outer layer is designed to provide external characteristics, such as reduced air resistance or increased absorbability of electromagnetic radiation. When the substrate is a bone implant adapted to use in the human body, surface material is removed from the implant without stress on the adjoining material, and the process provides fully dimensioned fillet radii at the base of the surface irregularities which is then adapted to receive the ingrowth of bone material when joined to bone during implantation. An irregular series of projections and depressions is formed to accommodate such ingrowth, providing a large surface area without any surface manipulations or additions.

Where the invention employs chemical etching, the surface is prepared through an etching process which utilizes the random application of a maskant and subsequent etching of the metallic substrate in areas unprotected by the maskant This etching process is repeated a number of times as necessitated by the amount and nature of the irregularities required for any particular application. Control of the strength of the etchant material, the temperature at which the etching process takes place and the time allotted for such an etching technique permit fine control over the resulting surface produced by the process. The number of repetitions of the etching process is also utilized to control the surface features.

The particular maskant and etchant utilized for a given attachment surface is dictated by the base metal utilized for the implant While a titanium implant is contemplated as the best mode of practice in the invention, it is to be specifically understood that any base metal may be utilized as the implanted material. A change in the base metal would necessitate a change in the maskant and etchant. No limitation is to be inferred from the selection of titanium in the detailed description following nor in the selection of the particular maskant and etchant chemistries.

While a method for removing such material is described in Wagner et al., U.S. Pat. Nos. 5,507,815 and 5,258,098, this methodology may be inappropriate for certain base materials utilized in the production of bone implants. Most notably, cobalt-chromium alloys present a particular challenge for material removal, primarily because of their high chemical inertness which makes them resistant to chemical etching. The surface of such an alloy is therefore preferably prepared through an electrochemical etching process which utilizes the random application of a maskant and subsequent electrochemical etching of the metallic substrate in areas unprotected by the maskant. This electrochemical etching process is repeated a number of times as necessitated by the amount and nature of the irregularities required for any particular application. Control of the composition, temperature, and flow rate of the electrolyte, the work gap between the cathodic tool and the attachment surface of the anodic workpiece, the voltage difference between the cathodic tool and the anodic workpiece, the specific amperage, the temperature at which the electrochemical etching process takes place, and the time allotted for electrochemical etching permit fine control over the resulting surface produced by the process. The number of repetitions of the electrochemical etching process is also utilized to control the surface features.

The particular maskant and the parameters of the electrochemical etching process utilized for a given attachment surface is dictated by the base metal utilized for the implant. While a cobalt-chromium alloy implant is contemplated as the best mode of practice in the invention, it is to be specifically understood that any base metal may be utilized as the implanted material. A change in the base metal may necessitate a change in the maskant, the electrolyte, and the parameters of the electrochemical etching process. No limitation is to be inferred from the selection of a cobalt-chromium alloy in the detailed description which follows nor in the selection of the particular maskant and of the particular parameters of the electrochemical etching process.

These and other advantages and features of the present invention will be more fully understood upon reference to the presently preferred embodiments thereof and to the appended drawings.

DESCRIPTION OF THE PREFERRED EMBODIMENTS

A. Chemical Etching Embodiments:

In describing the preferred embodiment of the invention when chemical etching is employed and the best mode of carrying the invention out, the drawings and description refer to the use of a titanium alloy base metal. While titanium is the preferred embodiment for the implantable material, a number of other alloys may be utilized. Each of these different alloys will require a different maskant and etchant composition. Other than cobalt chromium, no specific details are given in the specification regarding the use of these other metals and etchants. It is, however, considered to be well within the knowledge of an experienced practitioner in the art to select an etchant once a base alloy has been identified. Furthermore, for the purposes of clarity, certain repetitive elements in the drawings have not been numerically identified for each and every occurrence. For example, a number of maskant points are shown on the surface diagrams. It is considered apparent from the drawings that the maskant points and other surface features of the etched implant are repeated and are readily identifiable without the aid of numeric identification for each feature. Only representative features and maskant points have therefore been identified.

Figure 1:
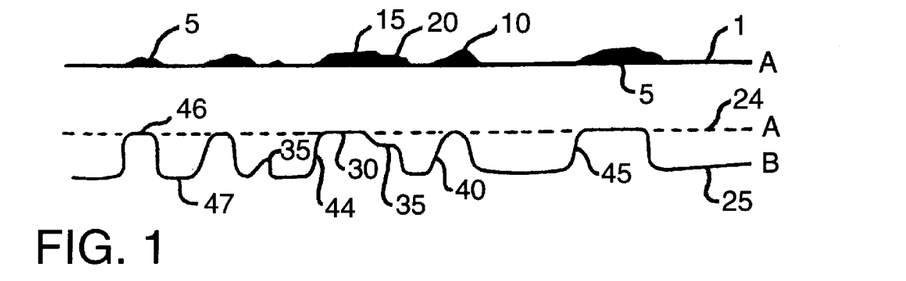
FIG. 1 is a diagrammatic representation of a first cycle of the etching process, illustrating a first surface having a maskant applied thereto and a second surface indicating the resultant surface after etching.

Referring now to FIG. 1, an unfinished surface 1 is provided which diagrammatically represents the exterior surface of the device to be implanted. The letter identifiers on the right margin of the drawings are intended to provide a quick reference to the relative levels of etching. Unfinished surface 1 at level A is generally smooth and comprised of titanium metal or alloy such as Ti-6Al-4Va. As stated herein, a cobalt chromium alloy is also contemplated. A maskant is applied to the surface of the implant which is to be etched in a random fashion. Several methods may be utilized to accomplish the random spattering of the maskant on the surface. Among these are manually applying the masint by brushing it using the tips of a hair-type brush or utilizing any type of shredded hair-like fibrous applicator dipped in the maskant material. Another method of application would be delivered in an air stream utilizing an air brush or paint gun.

The maskant must be chosen carefully in order to provide a substance which will cling tightly to the surface of the implant during manipulation of the implant and will also remain stable when the etchant solution is applied to the coated part. The maskant must also be removed with no residue once its function has been accomplished A particular problem encountered when utilizing maskants is the performance of the maskant at the boundaries of its application. The maskant should produce a sharply defined edge once the etching process has begun and not itself deteriorate during the etching process. This might permit partial degradation of the substrate in a masked area It should be noted, however, that some deterioration is found in any maskant use and does provide some of the particular surface features of the etched implant described later.

The surface 1 of the implant must be clean and grease-free and any oxidized material should be removed before the application of the maskant. This may be accomplished either mechanically, chemically or both. The surface may be cleaned mechanically utilizing a light abrasive blast of aluminum oxide particles or glass beads. Alternatively, blasting with any small solid particle which will not degrade the surface is contemplated A chemical agent such as methanol may be utilized alone or in conjunction with the blasting. Most maskants are very sensitive to the condition of the applied surface and both application and removal of the maskant may be affected by improper surface treatment. The maskant can be comprised of a number of materials including neoprene elastomers and isobutylene isoprene copolymers. The particular maskant should be selected based on the type of etchant utilized. The preferred maskant is AC-818C, an air-cured, general purpose, peelable coating produced by A.C. Products, Inc. of Placentia, Calif. The maskant is thinned utilizing perchlorethylene to 35–45 seconds utilizing a No. 5 Zahn cup. The maskant, if too thin, may be thickened to this viscosity by evaporation of the carrier. While the maskant is traditionally utilized in the 14–18 second range, it has been found that this thicker version produces superior results in terms of applying the maskant utilizing manual daubing or spray application techniques. It is to be specifically noted that the maskant is applied in a random spattered fashion allowing only a portion of the surface of the implant to be coated thereby. A random "polka dot" pattern is preferred in which each of the maskant points is of varying size and thickness when compared to the others. In some instances, the applied maskant may be partially abraded utilizing the grit blasting technique described previously for cleaning with an 80–120 mesh grit at 80–90 psi. to assist in providing an irregular maskant coating.

As shown in FIG. 1, a variety of applied maskant points 5 are illustrated. A particularly thick maskant agglomeration 10 is also illustrated. Other surface features of the applied maskant include an applied maskant plateau 15 and an applied maskant thin layer 20. It is desirable to achieve a variety of sizes and thicknesses of maskant in order to obtain the proper random finished surface. As will be seen later, each of these particular maskant surface features produces a somewhat different etched result. An optional step of drying the maskant at an elevated temperature is also contemplated. Four to five minutes at 200° F. is sufficient.

Referring now to the second illustration of FIG. 1, the etched result is illustrated, based on the applied maskant shown in the upper illustration. The unfinished surface indication line 24, shown as a chain, indicates the original level identified by the letter A at which the surface began. The first etched surface 25 identified by the letter B shows the resultant etched surface. While a number of etchants could be utilized, the particular chemistry adopted for the preferred embodiment utilizes a standard 30% nitric acid— 6% hydrofluoric acid combination which is commonly marketed and well known in the art. The etchant is applied at 110° F. for approximately 4 minutes to achieve a desired 0.008–0.010 inch etch depth. This time period or the strength of the etchant solution may be adjusted upwardly or downwardly to achieve a heavier or lighter etching. The etching is halted in a water bath or spray.

The maskant material may be removed in a variety of ways. The material may be removed mechanically or chemically. Depending on the size and number of coated objects, mechanical brushing or blasting of the maskant will peel it off. Additionally, the use of nitric acid is contemplated to dissolve the maskant material.

Referring again to the second illustration of FIG. 1, a number of surface features may be identified. A primary plateau 30 corresponds to the applied maskant plateau 15 illustrated in the top drawing. The heavy maskant coat completely protects the implant surface, preventing any metallic material from being removed at this point. A secondary plateau 35 corresponds to the thin layer 20 illustrated in the above drawing. The intermediate height of the secondary plateau between levels A and B indicates that the maskant performed for some period during the etching cycle but failed at an intermediate time allowing some of the alloy to be etched away. A small promontory, third from the left as shown in FIG. 1, also illustrates a small secondary plateau 35. Gradually sloped feature 40 corresponds to a gradually tapering maskant coverage which partially protects the underlying substrate during the etching cycle. A highly sloped feature 44 indicates a thicker maskant coating which enjoyed a highly defined perimeter before etching. A medium sloped feature 45 indicates a maskant condition intermediate the two previously described. The extremes of the etching are indicated by unetched level 46 and first etched level 47 which illustrate the effect of complete maskant coating versus no maskant coating. It should be noted that the base of each surface feature provides full dimensionally filleted radii.

Figure 2:
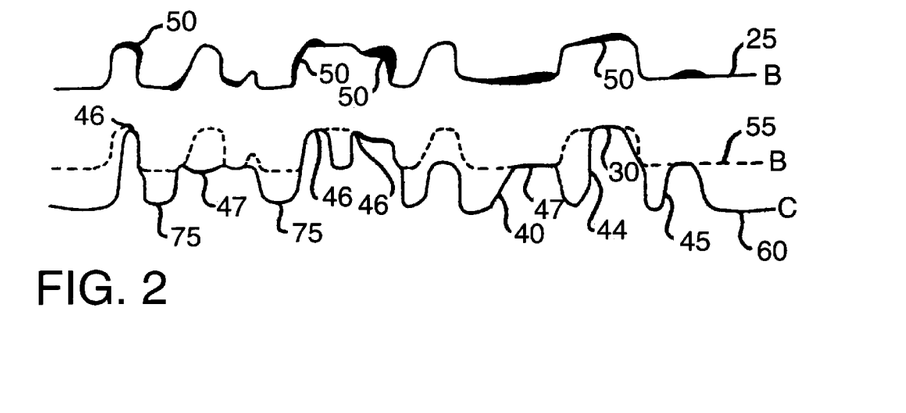
FIG. 2 is a diagrammatic representation of the second cycle of the etching process, illustrating the second surface illustrated in FIG. 1 having a maskant applied thereto and a resultant third surface prepared by etching the masked second surface.

FIG. 2 also employs two illustrations to display the effects of a second masking/etching cycle. The upper illustration corresponds to the second illustration of FIG. 1, the lowest extreme being found at the level indicated as B. The maskant is again applied to a clean and prepared surface in a random fashion according to the same techniques described with reference to FIG. 1. As before, a randomized pattern is preferable in which a wide variety of maskant surface features is achieved. Second applied maskant points 50 illustrate a variety of positions in which the maskant may be applied to the now irregular surface features of first etched surface 25.

Moving to the second illustration of FIG. 2, the first etched surface indication line 55 is shown in chain line to indicate the previous surface prior to the second etching cycle. The second etching cycle is performed under identical conditions as that described with reference to FIG. 1 to again achieve a 0.008–0.010 inch maximum etch. Second etched surface 60 is shown at level C, indicating a resultant etched surface. As previous described, the number of surface features are illustrated corresponding to the characteristics of the applied maskant. A highly sloped surface feature 44 corresponds again to a sharply defined and relatively thick application of maskant while a gradually sloped surface feature 40 corresponds to a gradually thinning maskant application. This feature is particularly visible in the two illustrations contained in FIG. 2 in which the gradual thinning of the maskant application is particularly exaggerated.

As can be seen in the second illustration of FIG. 2, three major levels of surface features are illustrated with a few intermediate features present to demonstrate the effects of partial maskant failure. A few points remain at unetched level 46 indicating maskant coverage during both etchant cycles. Some points are illustrated at first etched level 47 indicating maskant coverage during one of the two cycles, while points located at second etched level 75 have been exposed to the etchant during both of the etching cycles. The increasing level of complexity of surface forms is apparent with comparison between FIGS. 1 and 2.

Figure 3:
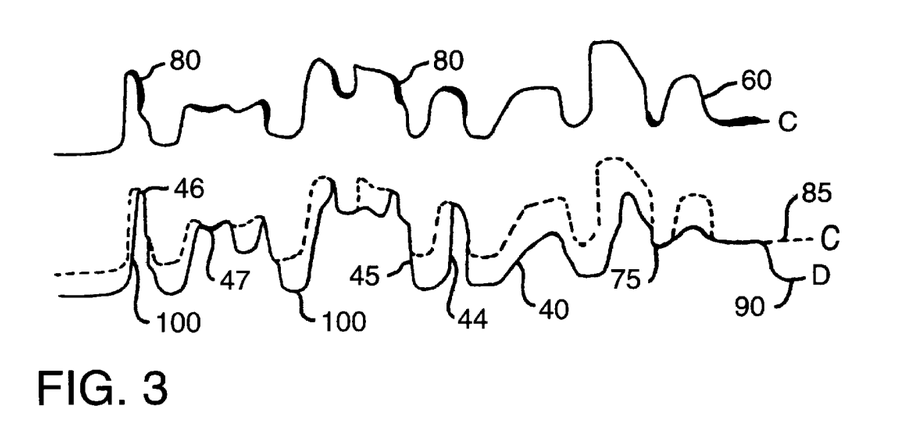
FIG. 3 is a diagrammatic representation of the third cycle of the etching process illustrating the resultant third etched surface of FIG. 2, also having a maskant applied thereto and a fourth surface prepared by etching the masked surface.

FIG. 3 is essentially a repetition of FIG. 2 having an upper illustration showing the application of third applied maskant points 80 to the now highly featured second etched surface 60 at level C. The increasing complexity of the surface of the etched device contributes also to the complexity of the maskant forms when applied to the irregular surface. The second illustration of FIG. 3 is shown to demonstrate the effect of a less rigorous etching cycle, being roughly one-half of the depth shown in FIGS. 1 and 2. The number and length of each etching cycle is purely dependent on the complexity of features required by the application and may be performed by any order. As shown in the second illustration of FIG. 3, a gradually sloped surface feature 40 retains its gradually sloped character from one cycle to the next when not covered by a maskant. This is to illustrate the consistent and uniform attack on the surface by the etchant solution. Highly sloped surface feature 44 again illustrates the effect of a highly stable maskant agglomeration while medium sloped surface feature 45 again demonstrates an intermediate condition. As illustrated in the second drawing of FIG. 3, four major surface levels are illustrated. Points at unetched level 46 are still apparent although fewer in number and relatively rare. A number of plateaus remain at first etched level 47 and second etched level 75. Those areas which have been exposed during all three etchant cycles enjoy depressions at third etched surface 100 corresponding to level D in FIG. 3. These levels correspond to areas which have had coverage during all three cycles, two cycles, one cycle and no cycles, respectively. The result as shown by third etched surface 90 is of a highly non-uniform featured surface which, compared with its length, also exhibits a large surface area. The different levels of depression and protrusion are particularly adapted to permit the ingrowth of bone and to allow for a firm anchoring of the bone along the surface of the implant structure.

Figure 4:
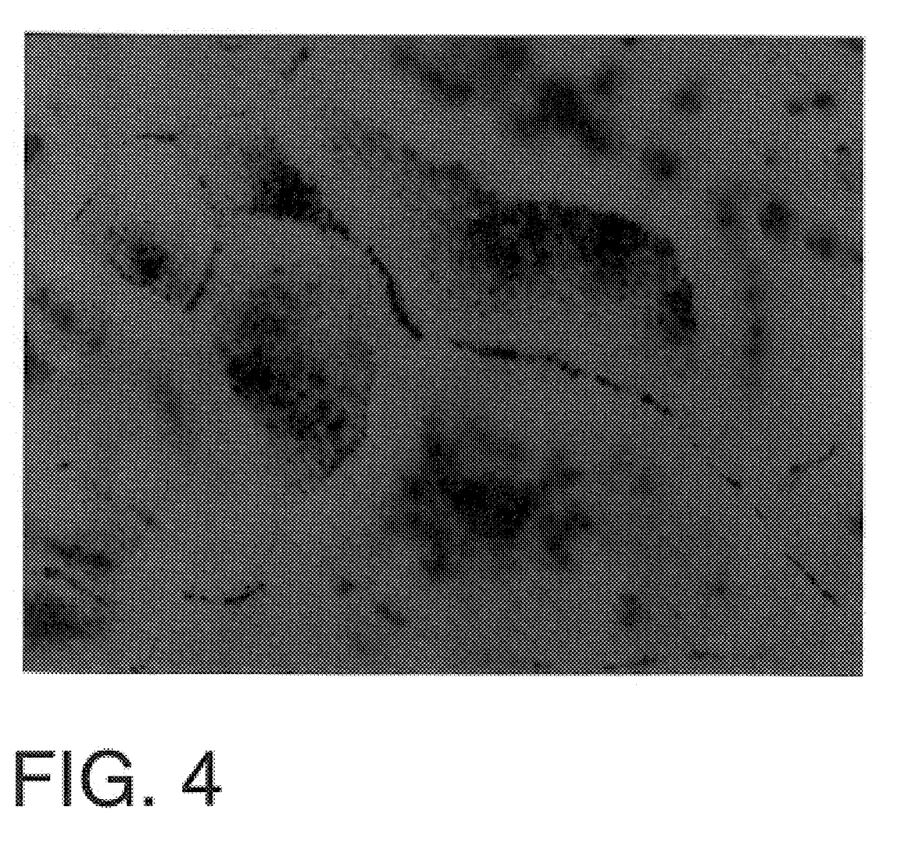
FIG. 4 is a photomicrograph of the chemically etched surface.

FIG. 4 illustrates a sample resultant surface. While specific identification of the surface features is difficult, a long ridge line is visible extending diagonally from upper left to lower right. A first level of three plateaus is visible at the center of the Figure, and lower level features extend outwardly in the upper right and lower left directions. All surface features are fully filleted and irregularly shaped to promote bone ingrowth.

B. Electrochemical Etching Embodiments:

In describing the preferred embodiment of the invention when electrochemical etching is employed and the best mode of carrying the invention out, the drawings and description refer to the use of a cobalt-chrornium alloy base metal. While cobalt-chromium alloy is the preferred embodiment for the implantable material, a number of other alloys may be utilized in connection with electrochemical etching. Each of these different alloys may require a different maskant and electrochemical etching conditions. While no specific details are given in the specification regarding the use of these other metals and electrochemical etching conditions, it is considered to be well within the knowledge of an experienced practitioner in the art to select the appropriate electrochemical etching conditions once a base alloy has been identified. Furthermore, for the purposes of clarity, certain repetitive elements in the drawings have not been numerically identified for each and every occurrence. For example, a number of maskant points are shown on the surface diagrams. It is considered apparent from the drawings that the maskant points and other surface features of the etched implant are repeated and are readily identifiable without the aid of numeric identification for each feature. Only representative features and maskant points have therefore been identified.

Referring now to FIG. 1, an unfinished surface 1 is provided which diagrammatically represents the exterior surface of a device, such as a bone implant, that is to be joined to a second material. The letter identifiers on the right margin of the drawings are intended to provide a quick reference to the relative levels of electrochemical etching. Unfinished surface 1 at level A is generally smooth and comprised of cobalt-chromium alloy such as the cobalt-28 chromium-6 molybdenum alloy described in Table 1. A maskant is applied to the surface of the device which is to be electrochemically etched in a random fashion. Several methods may be utilized to accomplish the random spattering of the maskant on the surface. Among these are manually applying the maskant by brushing it using the tips of a hair-type brush or utilizing any type of shredded hair-like fibrous applicator dipped in the maskant material. Another method of application would be delivered in an air stream utilizing an air brush or paint gun.

TABLE I

Composition of Cobalt-28 Chromium-6 Molybdenum Alloy

|  | minimum %* | maximum %* | tolerance +/− %* |
|---|---|---|---|
| Chromium | 26.0 | 30.0 | 0.30 |
| Molybdenum | 5 | 7 | 0.15 |
| Nickel | — | 1.0 | 0.05 |

TABLE I-continued

Composition of Cobalt-28 Chromium-6 Molybdenum Alloy

|  | minimum %* | maximum %* | tolerance +/- %* |
|---|---|---|---|
| Iron | — | 0.75 | 0.03 |
| Carbon | — | 0.35 | 0.02 |
| Silicon | — | 1.0 | 0.05 |
| Manganese | — | 1.0 | 0.03 |
| Nitrogen | — | 0.25 | 0.03 |
| Cobalt | balance | — | — |

*weight percent.

The maskant must be chosen carefully in order to provide a substance which will cling tightly to the surface of the device during manipulation of the device and will also remain stable when the etchant solution is applied to the coated part. The maskant must also be removed with no residue once its function has been accomplished. A particular problem encountered when utilizing maskants is the performance of the maskant at the boundaries of its application. The maskant should produce a sharply defined edge once the electrochemical etching process has begun and not itself deteriorate during the electrochemical etching process. This might permit partial degradation of the substrate in a masked area It should be noted, however, that some deterioration is found in any maskant use and does provide some of the particular surface features of the electrochemical etched device described later.

The surface 1 of the device must be clean and grease-free and any oxidized material should be removed before the application of the maskant This may be accomplished either mechanically, chemically or both. The surface may be cleaned mechanically utilizing a light abrasive blast of 80 to 120 grit aluminum oxide particles or glass beads. Alternatively, blasting with any small solid particle which will not degrade the surface is contemplated. All blasting residue is to be removed by brushing. A chemical agent such as acetone may be utilized alone or in conjunction with the blasting to clean the surface 1. Most maskants are very sensitive to the condition of the applied surface and both application and removal of the maskant may be affected by improper surface treatment The maskant can be comprised of a number of materials including neoprene elastomers and isobutylene isoprene copolymers. The preferred maskant for use with cobalt-chromium alloys is an alkaline soluble, air-curable phenol-formaldehyde resin maskant material such as Hysol ER1006 produced by The Dexter Corporation, Industry, Calif.

It is to be specifically noted that the maskant is applied in a random spattered fashion allowing only a portion of the surface of the device to be coated thereby. A random "polka dot" pattern is preferred in which each of the maskant points is of varying size and thickness when compared to the others. In some instances, the applied maskant may be partially abraded utilizing the grit blasting technique described previously for cleaning with an 80–120 mesh grit at 80–90 psi to assist in providing an irregular maskant coating.

The viscosity of the maskant should be adjusted to a level that promotes both the application of the maskant in a random spattered panern and the proper curing of the maskant. The maskant may be thinned to the optimum viscosity by the addition of its carrier fluid. If the maskant is too thin, the maskant may be thickened to a lower viscosity by evaporation of its carrier fluid. For the Hysol ER1006 maskant, the optimum viscosity is about 60–66 seconds as measured utilizing a No. 5 Zahn cup.

After the maskant has been applied in a random spattered pattern, it is cured. For example, the Hysol ER1006 maskant is preferably cured for a minimum of about 20 minutes at between about 200–250° F. and then air cooled to room temperature.

As shown in FIG. 1, a variety of applied maskant points 5 are illustrated. A particularly thick maskant agglomeration 10 is also illustrated. Other surface features of the applied maskant include an applied maskant plateau 15 and an applied maskant thin layer 20. It is desirable to achieve a variety of sizes and thicknesses of maskant in order to obtain the proper random finished surface. As will be seen later, each of these particular maskant surface features produces a somewhat different electrochemical etching result.

Figure 5:
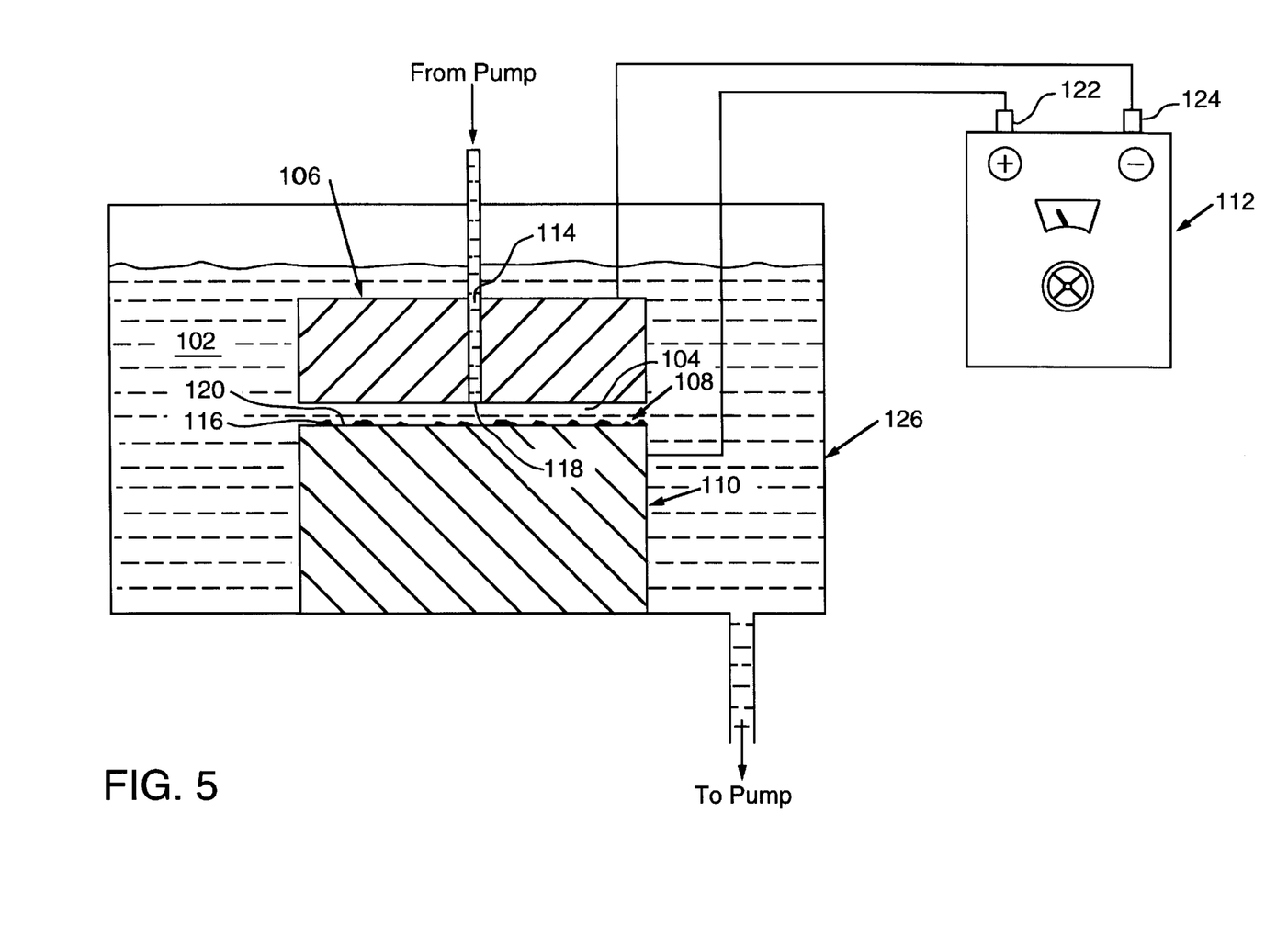
FIG. 5 is a diagrammatic representation, partially in cross section, of the arrangement of the elements of a typical electrochemical etching process.

FIG. 5 diagrammically shows the arrangement of the elements of a typical electrochemical etching process. After the maskant material has been applied and cured, the exposed portion 120 of the attachment surface 108 of workpiece 110 is ready to be electrochemically etched. The exposed portion 120 of the attachment surface 108 is that portion of the attachment surface 108 which is not covered by maskant deposits 116. A tank 126 may be used to submerge the tooling 106 and the workpiece 110 under an electrolyte fluid 102. The electrolyte fluid 102 fills the work gap 104 between the tooling 106 and the attachment surface 108 of the workpiece 110. The electrolyte fluid 102 is pumped at controlled rate through a passageway 114 in the tooling 106 and out through an orifice 118 into the work gap 104. The tooling 106 is in electrical connection with the negative terminal 124 of a direct current power supply 112 and thus becomes the cathode of the electrochemical etching process. The workpiece 110 is in electrical connection with the positive terminal 122 of the same direct current power supply 112 and thus becomes the anode of the electrochemical etching process.

The electrolyte fluid 102 for electrochemically etching a cobalt-chromium alloy is preferably a solution containing the proportions of one pound each of NaCl and $NaNO_3$ dissolved in one gallon of water. One skilled in the art of electrochemically etching metals will recognize and employ the appropriate electrolyte fluid 102 to be used for the type of metal of a particular workpiece 110. Control of the flow rate of the electrolyte fluid 102 through the work gap 104 is important because the electrolyte fluid 104 must adequately remove both the heat and the reaction products of the electrochemical process. The optimum flow rate level is related to the amount of current employed. Higher ratios of flow rate to current give better removal of heat and reaction products. For the electrochemical etching a cobalt-chromium alloy, for example, the electrolyte fluid 102 should flow through the work gap 104 at a rate of about 0.15–0.5 gallons per minute per 100 amps and have a temperature of between about 100–130° F. One skilled in the art of electrochemically etching metals will be able to determine the proper values of these parameters to use with a particular application.

The tooling 106 may be made from any material suitable for use in electrochemical etching such as copper, nickel, or an alloy of tungsten-copper. The tooling 106 should be configured so that the work gap 104 between the tooling 106 and the attachment surface 108 is substantially uniform. This is accomplished by making the tooling 106 substantially conformal to the attachment surface 108. Preferably, the work gap 104 is between about 0.020–0.250 inches, more particularly between about 0.060–0.120 inches. One skilled in the art of electrochemically etching metal will be able to determine the proper work gap 104 to use for a particular application. A direct current voltage difference between the tooling 106 and the attachment surface 108 of between about 8V–24V and a specific amperage of at least about 50 amps per square inch of exposed portion 120 of the attachment surface 108 are to be maintained during the electrochemical etching of a cobalt-chromium workpiece 110. Preferably, the direct current voltage difference between the tooling 106 and the attachment surface 108 is between about 12–18V and the specific amperage is about 75–120 amps per square inch of exposed portion 120 of the attachment surface 108. The values of these parameters for use with other materials are readily determinable by one skilled in the art of electrochemical etching metals. The stated conditions will produce a metal removal rate of about 0.003 inch per minute when the workpiece 110 material is a cobalt-chromium alloy.

Referring now to the second illustration of FIG. 1, the electrochemically etched result is illustrated, based on the applied maskant shown in the upper illustration. The unfinished surface indication line 24, shown as a chain, indicates the original level identified by the letter A at which the surface began. The first electrochemically etched surface 25 identified by the letter B shows the resultant electrochemically etched surface. The electrochemical etching is continued until a desired etch depth of about 0.001–0.010 inch is achieved. Preferably, the etching is continued until a desired etch depth of about 0.002–0.007 inches is achieved. The time period and other parameters of the electrochemical etching process, particular the specific amperage, may be adjusted upwardly or downwardly to achieve a heavier or lighter etching. The electrochemical etching process is halted by removing the voltage difference between the tooling 106 and the workpiece 110.

The maskant material on the attachment surface 106 is removed after each electrochemical etching step. The maskant material may be removed in a variety of ways. The maskant material may be removed mechanically or chemically. Depending on the size and number of coated objects, mechanical brushing or blasting of the maskant may peel it off. In the preferred embodiment of the invention using a cobalt-chromium alloy workpiece and the Hysol ER1006 maskant material, the workpiece is immersed in an aqueous solution of an alkaline cleaner to dissolve the maskant material. Preferably, the temperature of the alkaline cleaner solution is between about 80–145°F. The immersion time is about 5 to 10 minutes or until the maskant is removed. Water blasting is employed to remove any clinging maskant material which was softened by the alkaline cleaning solution.

Preferably, the masking/electrochemical etching process is repeated three times, though useful attachment surfaces may be obtained through the use of fewer and more numerous cycles. The amount of material removed during each cycle is to be determined by the particular application. Preferably, substantially the same amount of material, as measured by depth of material removal, is removed in each cycle. When multiple masking/electrochemical etching cycles are employed, it is preferable that the attachment surface 106 be blasted with 80 to 120 mesh alumina grit prior to the application of the maskant material so as to promote the adhesion of the maskant material.

Referring again to the second illustration of FIG. 1, a number of surface features may be identified. A primary plateau 30 corresponds to the applied maskant plateau 15 illustrated in the top drawing. The heavy maskant coat completely protects the device surface, preventing any metallic material from being removed at this point A secondary plateau 35 corresponds to the thin layer 20 illustrated in the above drawing. The intermediate height of the secondary plateau between levels A and B indicates that the maskant performed for some period during the electrochemical etching cycle but failed at an intermediate time allowing some of the alloy to be etched away. A small promontory, third from the left as shown in FIG. 1, also illustrates a small secondary plateau 35. Gradually sloped feature 40 corresponds to a gradually tapering maskant coverage which partially protects the underlying substrate during the electrochemical etching cycle. A highly sloped feature 44 indicates a thicker maskant coating which enjoyed a highly defmed perimeter before the electrochemical etching. A medium sloped feature 45 indicates a maskant condition intermediate the two previously described. The extremes of the electrochemical etching are indicated by unetched level 46 and first electrochemically etched level 47 which illustrate the effect of complete maskant coating versus no maskant coating. It should be noted that the base of each surface feature provides full dimensionally filleted radii.

FIG. 2 also employs two illustrations to display the effects of a second masking/electrochemical etching cycle. The upper illustration corresponds to the second illustration of FIG. 1, the lowest extreme being found at the level indicated as B. The maskant is again applied to a clean and prepared surface in a random fashion according to the same techniques described with reference to FIG. 1. As before, a randomized pattern is preferable in which a wide variety of maskant surface features is achieved. Second applied maskant points 50 illustrate a variety of positions in which the maskant may be applied to the now irregular surface features of first electrochemically etched surface 25.

Moving to the second illustration of FIG. 2, the first electrochemically etched surface indication line 55 is shown in chain line to indicate the previous surface prior to the second electrochemical etching cycle. The second electrochemical etching cycle is performed under identical conditions as that described with reference to FIG. 1 to again achieve an approximately 0.001–0.010 inch electrochemical etch. Second electrochemically etched surface 60 is shown at level C, indicating a resultant electrochemically etched surface. As previous described, the number of surface features are illustrated corresponding to the characteristics of the applied maskant. A highly sloped surface feature 44 corresponds again to a sharply defmed and relatively thick application of maskant while a gradually sloped surface feature 40 corresponds to a gradually thinning maskant application. This feature is particularly visible in the two illustrations contained in FIG. 2 in which the gradual thinning of the maskant application is particularly exaggerated.

As can be seen in the second illustration of FIG. 2, three major levels of surface features are illustrated with a few intermediate features present to demonstrate the effects of partial maskant failure. A few points remain at unetched level 46 indicating maskant coverage during both electrochemical etching cycles. Some points are illustrated at first electrochemically etched level 47 indicating maskant coverage during one of the two cycles, while points located at second electrochemically etched level 75 have been exposed to the electrochemical etching process during both of the electrochemical etching cycles. The increasing level of complexity of surface forms is apparent with comparison between FIGS. 1 and 2.

FIG. 3 is essentially a repetition of FIG. 2 having an upper illustration showing the application of third applied maskant points 80 to the now highly featured second electrochemically etched surface 60 at level C. The increasing complexity of the surface of the electrochemically etched device contributes also to the complexity of the maskant forms when applied to the irregular surface. The second illustration of FIG. 3 is shown to demonstrate the effect of a less intense electrochemical etching cycle, being roughly one-half of the depth shown in FIGS. 1 and 2. The number and intensity of each electrochemical etching cycle is dependent on the complexity of features required by the application and may be performed in any order. As shown in the second illustration of FIG. 3, a gradually sloped surface feature 40 retains its gradually sloped character from one cycle to the next when not covered by a maskant. This is to illustrate the consistent and uniform attack on the surface by the electrochemical etching process. Highly sloped surface feature 44 again illustrates the effect of a highly stable maskant agglomeration while medium sloped surface feature 45 again demonstrates an intermediate condition. As illustrated in the second drawing of FIG. 3, four major surface levels are illustrated. Points at unetched level 46 are still apparent although fewer in number and relatively rare. A number of plateaus remain at first electrochemically etched level 47 and second electrochemically etched level 75. Those areas which have been exposed during all three electrochemical etch process cycles enjoy depressions at third electrochemically etched surface 100 corresponding to level D in FIG. 3. These levels correspond to areas which have had coverage during all three cycles, two cycles, one cycle and no cycles, respectively. The result, as shown by third electrochemically etched surface 90, is a highly non-uniform featured surface which, compared with its length, also exhibits a large surface area. The different levels of depression and protrusion are particularly adapted to permit the ingrowth of bone and to allow for a fmn anchoring of the bone along the surface of an implant structure. The different levels of depression and protrusions are also particular adapted to permit the inflow and anchoring of adhesives.

Figure 6:
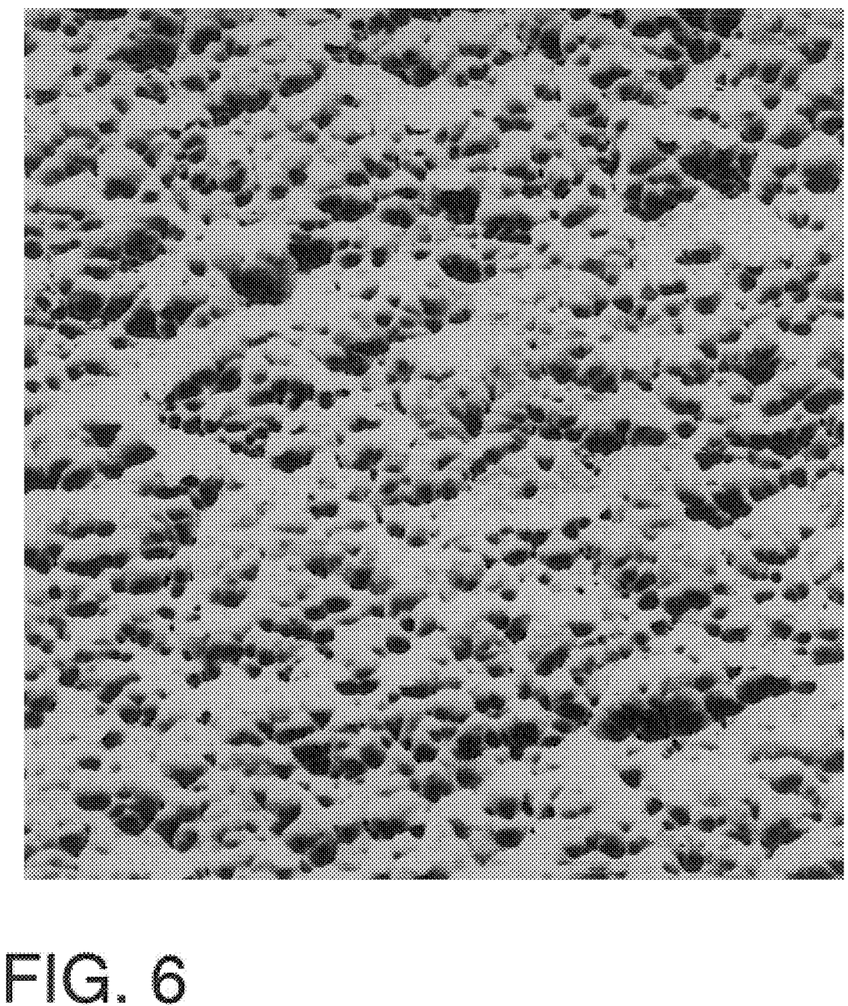
FIG. 6 is a photomicrograph of the electrochemically etched surface.

FIG. 6 illustrates a sample resultant surface. All surface features are fully filleted and irregularly shaped to promote bone ingrowth and the inflow of adhesives.

While present preferred embodiments of the invention are described, it is to be distinctly understood that the invention is not limited thereto but may be otherwise embodied and practiced within the scope of the following claims.

What is claimed is:

1. An irregular exterior surface portion on a substrate material which is particularly adapted to be joined to a second material, the surface portion to be so joined comprising a plurality of randomly sized and spaced protrusions located upon said surface portion, produced by the method comprising the steps of:
 a) masking said surface portion in a random pattern with a maskant material, such that less than the entire surface portion is covered thereby;
 b) electrochemically etching said surface portion such that said substrate material is removed thereby in areas uncovered by said maskant material, and areas covered by said maskant material are left intact;
 c) removing said maskant material; and
 d) repeating said masking, electrochemically etching and removing steps upon said surface portion until a desired surface irregularity is achieved.

2. An irregular exterior surface portion on a substrate material, produced by the method as described in claim 1, further comprising the additional preparatory step of cleaning said surface portion.

3. An irregular exterior surface portion on a substrate material, produced by the method as described in claim 2, wherein said cleaning step is accomplished by impinging small solid particles on said surface portion.

4. An irregular exterior surface portion on a substrate material, produced by the method as described in claim 3, wherein said small solid particles are one of aluminum oxide particles and glass beads.

5. An irregular exterior surface portion on a substrate material, produced by the method as described in claim 2, wherein said cleaning step utilizes acetone as a cleanig agent.

6. An irregular exterior surface portion on a substrate material, produced by the method as described in claim 5, wherein said cleaning step utilizes acetone and the impinging of small solid particles.

7. An irregular exterior surface portion on a substrate material, produced by the method as described in claim 1, further comprising the additional step, following said masking step, of partially abrading the applied maskant by impinging small solid particles thereon.

8. An irregular exterior surface portion on a substrate material, produced by the method as described in claim 7, wherein said small solid particles are one of aluminum oxide and glass beads.

9. An irregular exterior surface portion on a substrate material, produced by the method as described in claim 1, wherein said maskant material is soluble in an alkaline solution.

10. An irregular exterior surface portion on a substrate material, produced by the method as described in claim 9, wherein said maskant material comprises a phenol-formaldehyde resin.

11. An irregular exterior surface portion on a substrate material, produced by the method as described in claim 1, her comp rising the additional step, after said masking step, of drying the maskant material at an elevated temperature.

12. An irregular exterior surface portion on a substrate material, produced by the method as described in claim 11, said drying step occurring at about 200–250° F. for a time of at least about 20 minutes.

13. An irregular exterior surface portion on a substrate material, produced by the method as described in claim 1, wherein said removing step utilizes a mechanical abrasive technique for removal of the maskant material.

14. An irregular exterior surface portion on a substrate material, produced by the method as described in claim 13, wherein said maskant material is removed by completely abrading the maskant material by impinging small solid particles thereon.

15. An irregular exterior surface portion on a substrate material, produced by the method as described in claim 1, wherein said removing step is accomplished utilizing a chemical agent.

16. An irregular exterior surface portion on a substrate material, produced by the method as described in claim 15, wherein said chemical agent is an alkaine solution.

17. An irregular exterior surface portion on a substrate material, produced by the method as described in claim 1, wherein said electrochemical etching step is performed to achieve an etch level range of about 0.001–0.010 inches.

18. An irregular exterior surface portion on a substrate material, produced by the method as described in claim 17, wherein said electrochemical etching step is performed to achieve an etch level range of about 0.002–0.007 inches.

19. An irregular exterior surface portion on a substrate material, produced by the method as described in claim 1, wherein said maskant material has a viscosity of about 60–66 seconds as measured on a No. 5 Zahn cup.

20. An irregular exterior surface portion on a substrate material, produced by the method as described in claim 1, wherein said electrochemical etching step further comprises using conformal tooling and using a substantially uniform work gap between said conformal tooling and said surface portion.

21. An irregular exterior surface portion on a substrate material, produced by the method as described in claim 20, wherein said work gap is between about 0.020–0.250 inches.

22. An irregular exterior surface portion on a substrate material, produced by the method as described in claim 21, wherein said work gap is between about 0.060–0.120 inches.

23. An irregular exterior surface portion on a substrate material, produced by the method as described in claim 20, wherein there is a voltage difference between said conformal tooling and said surface portion, said voltage difference being about 8–24 Volts DC.

24. An irregular exterior surface portion on a substrate material, produced by the method as described in claim 23, wherein said voltage difference is about 12–18 Volts DC.

25. An irregular exterior surface portion on a substrate material, produced by the method as described in claim 20, further comprising using an electrolyte fluid in said work gap.

26. An irregular exterior surface portion on a substrate material, produced by the method as described in claim 25, wherein said electrolyte fluid comprises a solution of water, NaCl, and NaNO$_3$.

27. An irregular exterior surface portion on a substrate material, produced by the method as described in claim 25, wherein said electrolyte fluid has a flow rate, said flow rate being between about 0.15–0.50 gallons per minute per 100 amperes.

28. An irregular exterior surface portion on a substrate material, produced by the method as described in claim 25, said electrolyte fluid having a temperature of between about 100–130°F.

29. An irregular exterior surface portion on a substrate material, produced by the method as described in claim 1, wherein said electrochemical etching step includes using an electric current, said electric current having a specific amperage of at least about 50 amperes per square inch of said surface area uncovered by said maskant material.

30. An irregular exterior surface portion on a substrate material, produced by the method as described in claim 29, wherein said electric current has a specific amperage of between about 75–125 amperes per square inch of said surface area uncovered by said maskant material.

31. An irregular exterior surface portion on a substrate material, produced by the method as described in claim 1, wherein said substrate material is constructed from an alloy containing cobalt and chromium.

32. An irregular exterior surface portion on a substrate material, produced by the method as described in claim 1, wherein said substrate material is constructed from a cobalt-28 chromium-6 molybdenum alloy.

33. An irregular exterior surface portion on a substrate material, produced by the method as described in claim 1, wherein said substrate material is a bone implant which is adapted for use in the human body.

\* \* \* \* \*

UNITED STATES PATENT AND TRADEMARK OFFICE
CERTIFICATE OF CORRECTION

PATENT NO.     : 6,193,762 B1
DATED          : February 27, 2001
INVENTOR(S)    : Donald J. Wagner and Gary Reed It is certified that error appears in the above-identified patent and that said Letters Patent is hereby corrected as shown below:

<u>Title page,</u>
Item [57], ABSTRACT,
Line 6, delete "with is" and insert -- which is --.

<u>Column 1,</u>
Line 7, "continuation-in-part" should be -- division --.

<u>Column 5,</u>
Line 19, "masint" should be -- maskant --.

<u>Column 11,</u>
Line 31, delete "particular" and insert -- particularly --.
Line 36, "106" should be -- 108 --.

<u>Column 12,</u>
Lines 14 and 47, "defmed" should be -- defined --.
Line 44, delete "previous" and insert -- previously --.

<u>Column 13,</u>
Line 35, "fmn" should be -- firm --.

<u>Column 14,</u>
Line 11, "cleanig" should be -- cleaning --.
Line 36, "her comp rising" should be -- further comprising --.

<u>Column 16,</u>
Line 24, "claim 1" should be -- claim 31 --.

Signed and Sealed this

Eleventh Day of June, 2002

*Attest:*

*Attesting Officer*

JAMES E. ROGAN
*Director of the United States Patent and Trademark Office*